United States Patent
Peese et al.

(10) Patent No.: US 9,655,889 B2
(45) Date of Patent: May 23, 2017

(54) INHIBITORS OF HUMAN IMMUNODEFICIENCY VIRUS REPLICATION

(71) Applicant: ViiV HEALTHCARE UK (NO.5) LIMITED, Brentford, Middlesex (GB)

(72) Inventors: Kevin Peese, Haddam, CT (US); Zhongyu Wang, Tolland, CT (US); John F. Kadow, Wallingford, CT (US); B. Narasimhulu Naidu, Durham, CT (US)

(73) Assignee: ViiV Healthcare UK (No.5) Limited, Brentford, Middlesex (GB)

( * ) Notice: Subject to any disclaimer, the term of this patent is extended or adjusted under 35 U.S.C. 154(b) by 0 days.

(21) Appl. No.: 14/770,702

(22) PCT Filed: Mar. 10, 2014

(86) PCT No.: PCT/US2014/022354
§ 371 (c)(1),
(2) Date: Aug. 26, 2015

(87) PCT Pub. No.: WO2014/164409
PCT Pub. Date: Oct. 9, 2014

(65) Prior Publication Data
US 2016/0000771 A1    Jan. 7, 2016

Related U.S. Application Data

(60) Provisional application No. 61/780,179, filed on Mar. 13, 2013.

(51) Int. Cl.
| | |
|---|---|
| *C07D 401/02* | (2006.01) |
| *C07D 401/10* | (2006.01) |
| *A61K 31/437* | (2006.01) |
| *A61K 31/4353* | (2006.01) |
| *A61K 31/4545* | (2006.01) |
| *C07D 471/04* | (2006.01) |
| *A61K 45/06* | (2006.01) |

(52) U.S. Cl.
CPC .......... *A61K 31/4545* (2013.01); *A61K 45/06* (2013.01); *C07D 471/04* (2013.01)

(58) Field of Classification Search
CPC .. C07D 401/02; C07D 401/10; A61K 31/437; A61K 31/4353
USPC .......................................... 546/121; 514/300
See application file for complete search history.

(56) References Cited

U.S. PATENT DOCUMENTS 5,360,796 A * 11/1994 Hansen, Jr. ........... C07F 9/6561
514/217.07

* cited by examiner

*Primary Examiner* — Niloofar Rahmani
(74) *Attorney, Agent, or Firm* — Robert H. Brink; R. Steve Thomas; Edward R. Gimmi

(57) ABSTRACT

The disclosure generally relates to compounds of formula (I), including compositions and methods for treating human immunodeficiency virus (HIV) infection. The disclosure provides novel inhibitors of HIV, pharmaceutical compositions containing such compounds, and methods for using these compounds in the treatment of HIV infection.

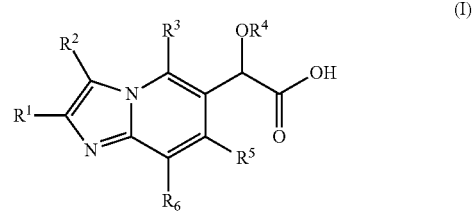

15 Claims, No Drawings

INHIBITORS OF HUMAN IMMUNODEFICIENCY VIRUS REPLICATION

CROSS-REFERENCE TO RELATED APPLICATIONS

This application claims priority to U.S. Provisional Patent Application Ser. No. 61/780,179, filed Mar. 13, 2013, which is incorporated by reference in its entirety.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that as many as 33.3 million people worldwide are infected with the virus (UNAIDS Report on the Global AIDS Epidemic 2010). In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The non-nucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: However, the effect is only temporary as the virus readily develops resistance to all known agents used as monotherapy. On the other hand, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. N. Engl. J. Med. 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2007131350, WO2009062285, WO2009062288, WO2009062289, WO2009062308, WO2010130034, WO2010130842, WO2011015641, WO2011076765, WO2012003497, WO2012003498, WO2012033735, WO2012065963 and WO2012066442.

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I

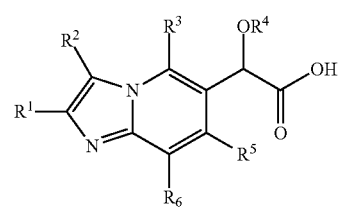

where:
$R^1$ is —CON($R^7$)($R^8$), —NHSO$R^7$, or ($R^7$)Ar$^2$
$R^2$ is hydrogen or alkyl;
$R^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;
or $R^3$ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;
$R^4$ is alkyl or haloalkyl;
$R^5$ is hydrogen or alkyl;
$R^6$ is hydrogen or alkyl;
$R^7$ is (Ar$^1$)alkyl;
$R^8$ is hydrogen or alkyl;
Ar$^1$ is phenyl substituted with 0-3 substituents selected from halo, cyano, alkyl, haloalkyl, alkoxy, haloalkoxy, and alkenyloxy; and $Ar^2$ is pyrrolyl, furanyl, thienyl, pyrazolyl, isoxazolyl, isothiazolyl, imidazolyl, oxazolyl, thiazolyl, triazolyl, oxadiazolyl, or thiadiazolyl, and is substituted with 0-3 substituents selected from halo, cyano, alkyl, haloalkyl, alkoxy, haloalkoxy, and alkenyloxy;

or a pharmaceutically acceptable salt thereof.

Another aspect of the invention is a compound of Formula I where $R^1$ is —CON($R^7$)($R^8$); $R^2$ is hydrogen or alkyl; $R^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl; or $R^3$ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl; $R^4$ is alkyl or haloalkyl; $R^5$ is hydrogen or alkyl; $R^6$ is hydrogen or alkyl; $R^7$ is ($Ar^1$)alkyl; $R^8$ is hydrogen or alkyl; and $Ar^1$ is phenyl substituted with 0-3 substituents selected from halo, cyano, alkyl, haloalkyl, alkoxy, haloalkoxy, and alkenyloxy; or a pharmaceutically acceptable salt thereof.

Another aspect of the invention is a compound of Formula I where $R^1$ is —CON($R^7$)($R^8$); $R^2$ is hydrogen; $R^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl; or $R^3$ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl; $R^4$ is alkyl or haloalkyl; $R^5$ is alkyl; $R^6$ is hydrogen; $R^7$ is ($Ar^1$)alkyl; $R^8$ is hydrogen; and $Ar^1$ is phenyl substituted with 0-3 substituents selected from halo, cyano, alkyl, haloalkyl, alkoxy, haloalkoxy, and alkenyloxy; or a pharmaceutically acceptable salt thereof.

Another aspect of the invention is a compound of Formula I where $R^2$ is hydrogen, $R^4$ is alkyl, $R^5$ is alkyl, and $R^6$ is hydrogen.

Another aspect of the invention is a compound of Formula I where $R^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl.

Another aspect of the invention is a compound of Formula I where $R^3$ is piperidinyl substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl.

Another aspect of the invention is a compound of Formula I where $R^3$ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl.

Another aspect of the invention is a compound of Formula I where $R^4$ is alkyl. Another aspect of the invention is a compound of Formula I where $R^5$ is alkyl.

Another aspect of the invention is a compound of Formula I where where $R^7$ is ($Ar^1$)$CH_2$ and $R^8$ is hydrogen.

For a compound of Formula I, the scope of any instance of a variable substituent, including $R^1$, $R^2$, $R^3$, $R^4$, $R^5$, $R^6$, $R^7$, $R^8$, $Ar^1$, and $Ar^2$, can be used independently with the scope of any other instance of a variable substituent. As such, the invention includes combinations of the different aspects.

Unless specified otherwise, these terms have the following meanings "Alkyl" means a straight or branched alkyl group composed of 1 to 6 carbons. "Alkenyl" means a straight or branched alkyl group composed of 2 to 6 carbons with at least one double bond. "Alkylene" means a straight or branched divalent alkyl group composed of 1 to 6 carbons. "Alkenylene" means a straight or branched divalent alkene group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes fluoro, chloro, bromo, and iodo. "Halo" includes all halogenated isomers from monohalo substituted to perhalo substituted in substituents defined with halo, for example, "Haloalkyl" and "haloalkoxy", "halophenyl", "halophenoxy." "Aryl" includes carbocyclic and heterocyclic aromatic substituents. Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereromers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV replication. A recombinant NL-Rluc virus was constructed in which a section of the nef gene from NL4-3 was replaced with the Renilla Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv in 293T cells using the LipofectAMINE PLUS kit from Invitrogen (Carlsbad, Calif.) according to the manufacturer, and the pseudotype virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. This provides a simple and easy method for quantitating the extent of virus growth and consequently, the antiviral activity of test compounds. Luciferase was quantitated using the Dual Luciferase kit from Promega (Madison, Wis.).

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press.1990). The anti-viral activity of compounds was evaluated under three serum conditions, 10% FBS, 15 mg/ml human serum albumin/10% FBS or 40% human serum/5% FBS, and the results from at least 2 experiments were used to calculate the $EC_{50}$ values. Results are shown in Table 1. Activity equal to A refers to a compound having an $EC_{50}$ <100 nM, while B and C denote compounds having an $EC_{50}$ between 100 nM and 1 uM (B) or >1 uM (C).

TABLE 1

| Example | $EC_{50}$ µM |
|---|---|
| 1 | 0.008 |
| 2 | 0.002 |
| 3 | 0.021 |
| 4 | 0.003 |
| 5 | 0.008 |
| 6 | 0.013 |
| 7 | 0.034 |
| 8 | 3.3 |
| 9 | 6.03 |

Pharmaceutical Composition and Methods of Use

The compounds of this invention inhibit HIV replication. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; and "DIEA" for diisopropylethylamine.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds of this invention can be synthesized from an appropriately substituted heterocycle I-1 according to Scheme I.

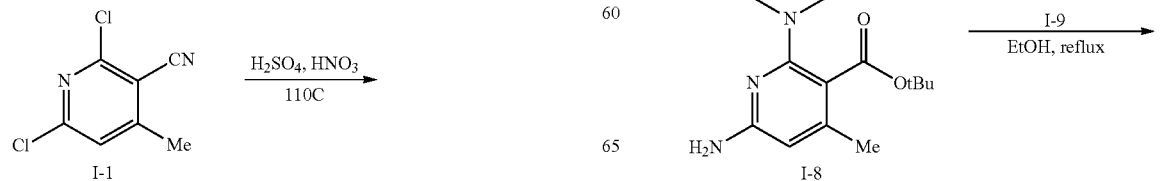

-continued
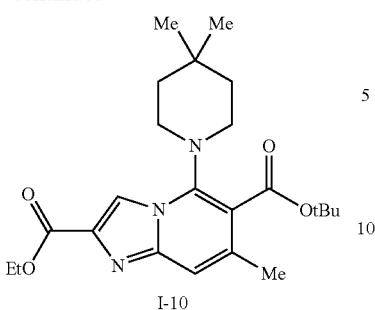
Some compounds of this invention can be prepared by the methods outlined in the Scheme II.
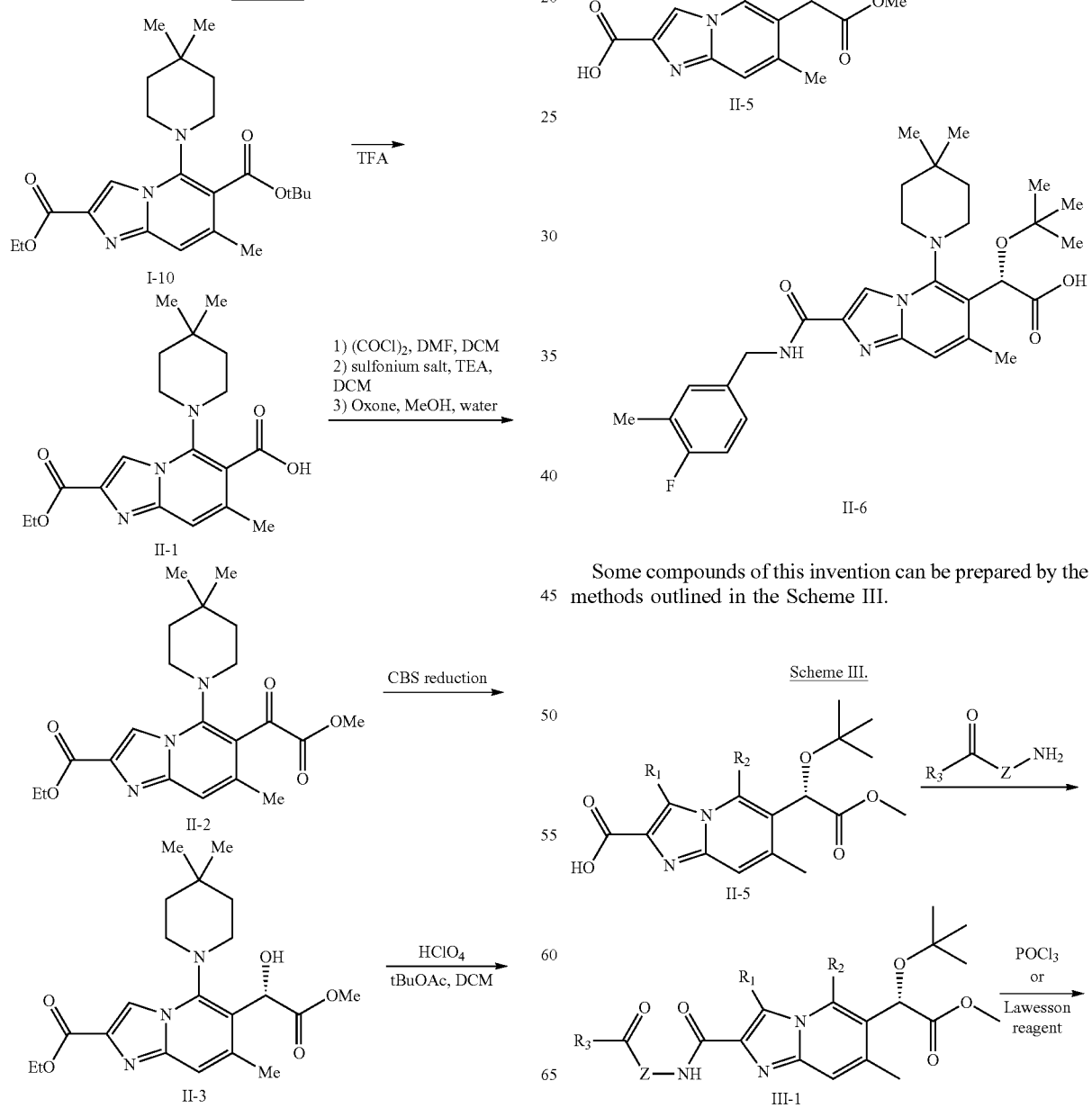
Some compounds of this invention can be prepared by the methods outlined in the Scheme III.

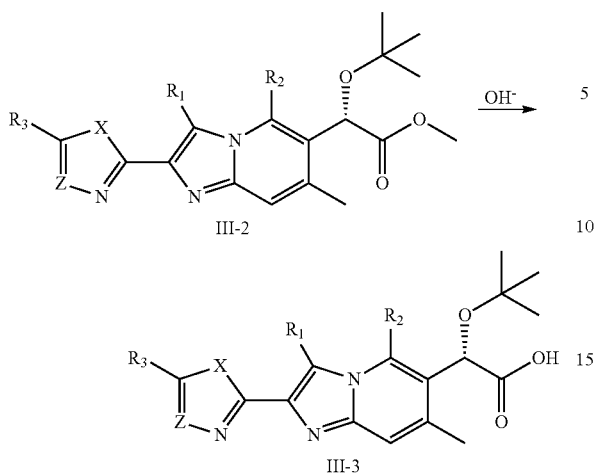

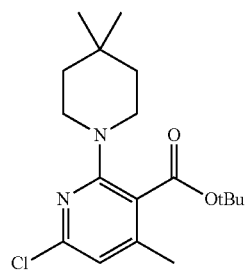

Intermediate 3 tert-Butyl 6-chloro-2-(4,4-dimethylpiperidin-1-yl)-4-methylnicotinate: To a solution of tert-butyl 2,6-dichloro-4-methylnicotinate (11.93 g, 45.4 mmol, 1 equiv) in DCE (228 mL) was added 4,4-dimethylpiperidine (7.21 g, 63.7 mmol, 1.4 equiv) and DIPEA (11.1 mL, 63.7 mmol, 1.4 equiv). The reaction was heated to reflux for 2 h, at which point it appears stalled at ~40% conversion. The solution was concentrated in vacuo. The residue was taken up in DMF (228 mL) and more 4,4-dimethylpiperidine (7.21 g, 63.7 mmol, 1.4 equiv) and DIPEA (11.1 mL, 63.7 mmol, 1.4 equiv) were added. Heat to 80° C. for 18 h. LCMS indicated ~70% conversion. Remove from heat and add to saturated aqueous sodium bicarbonate solution. This was extracted with ether (×2). The combined ether extracts were dried (MgSO$_4$) and concentrated in vacuo. The crude product was purified via flash silica gel chromatography (0-100% DCM/hexane) to provide the product (6.73 g, 44%) as a yellow solid. $^1$H NMR (400 MHz, CDCl$_3$) δ 6.55 (s, 1H), 3.41-3.33 (m, 4H), 2.27 (s, 3H), 1.59 (s, 9H), 1.48-1.41 (m, 4H), 0.99 (s, 6H); LCMS (ESI, M+1): 339.25.

The compounds described herein were purified by the methods known to those skilled in art by normal phase column chromatography on silica gel column using appropriate solvent systems. Preparative HPLC purifications mentioned in this experimentation section were carried out by gradient elution on C18 prep-columns (5 μm) using either mobile phase A: 9:1 H$_2$O/acetonitrile with 10 mM NH$_4$OAc and mobile phase B : A: 9:1 acetonitrile/H$_2$O with: 10 mM NH$_4$OAc or mobile phase A: 95:5 H$_2$O/MeOH with 20 mM NH$_4$OAc and mobile phase B: 95:5 MeOH/H$_2$O with 20 mM NH$_4$OAc.

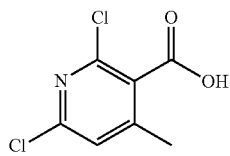

Intermediate 1

2,6-Dichloro-4-methylnicotinic acid: Prepared from commercially available 2,6-dichloro-4-methylnicotinonitrile following procedure in U.S. Pat. No. 6,677,352 (2004).

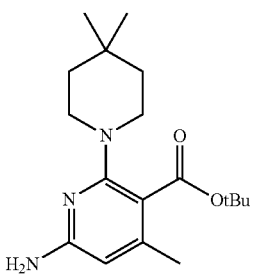

Intermediate 4 tert-Butyl 6-amino-2-(4,4-dimethylpiperidin-1-yl)-4-methylnicotinate: A solution of tert-butyl 6-chloro-2-(4,4-dimethylpiperidin-1-yl)-4-methylnicotinate (1.0 g, 2.95 mmol, 1 equiv), benzophenone imine (0.59 mL, 3.54 mmol, 1.2 equiv), Pd$_2$(dba)$_3$ (0.135 g, 0.148 mmol, 0.05 equiv), xantphos (0.171 g, 0.295 mmol, 0.10 equiv), and Cs$_2$CO$_3$ (2.31 g, 7.08 mmol, 2.4 equiv) in dioxane (30 mL deoxygenated by bubbling nitrogen through for 10 min) was heated to 90° C. After 20 h, remove from heat. Dilute with EtOAc and wash with water. EtOAc layer dried (Na$_2$SO$_4$) and concentrated in vacuo. This was taken up in MeOH (25 mL) and sodium acetate (0.73 g, 8.85 mmol, 3 equiv) and hydroxylamine hydrochloride (0.41 g, 5.90 mmol, 2 equiv) were added. The reaction turned very dark. After 1 h, the reaction was added to 1 N NaOH and extracted with DCM (×3). The combined DCM extracts were dried (Na$_2$SO$_4$) and concentrated in vacuo. The crude product was purified via flash silica gel chromatography (0-40% EtOAc/hexane) to provide the product (0.76 g, 81%) as a yellow solid. $^1$H

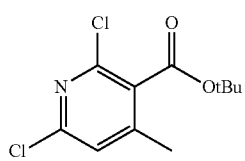

Intermediate 2 tert-Butyl 2,6-dichloro-4-methylnicotinate: To a solution of 2,6-dichloro-4-methylnicotinic acid (1.00 g, 4.85 mmol, 1 equiv) in tent-butyl acetate (24 mL) was added 70% perchloric acid (0.88 mL, 14.56 mmol, 3 equiv). After 1 h, reaction was diluted with DCM, washed cautiously with saturated aqueous sodium bicarbonate solution, dried (Na$_2$SO$_4$), and concentrated in vacuo to provide the product (1.21 g, 95%) as a pale yellow oil. $^1$H NMR (400 MHz, CDCl$_3$) δ 7.15 (s, 1H), 2.37 (d, J=0.5 Hz, 3H), 1.62 (s, 9H); LCMS (ESI, M+1): 262.1.

NMR (400 MHz, CDCl3) δ 5.77 (d, J=0.5 Hz, 1H), 4.22 (s, 2H), 3.37-3.23 (m, 4H), 2.22 (d, J=0.5 Hz, 3H), 1.58 (s, 9H), 1.47-1.39 (m, 4H), 0.98 (s, 6H); LCMS (ESI, M+1): 320.3.

Intermediate 5

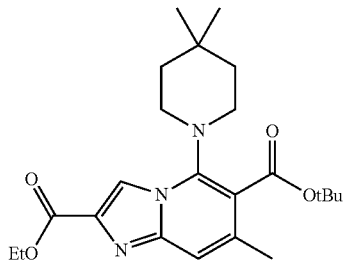

6-tent-butyl 2-ethyl 5-(4,4-dimethylpiperidin-1-yl)-7-methylimidazo[1,2-a]pyridine-2,6-dicarboxylate: A solution of tert-butyl 6-amino-2-(4,4-dimethylpiperidin-1-yl)-4-methylnicotinate (0.76 g, 2.38 mmol, 1 equiv) and ethyl bromopyruvate (0.40 mL, 2.85 mmol, 1.2 equiv) in EtOH (24 mL) was heated at 90° C. for 5 h. After cooling to ambient temperature, the reaction was added to saturated aqueous sodium bicarbonate solution and extracted with DCM (×3). The combined DCM extracts were dried (Na₂SO₄) and concentrated in vacuo. The crude product was purified via flash silica gel chromatography (0-100% EtOAc/hexane) to provide the product (0.61 g, 62%) as a yellow solid. ¹H NMR (400 MHz, CDCl₃) δ 8.14 (d, J=0.8 Hz, 1H), 7.23 (s, 1H), 4.48 (q, J=7.0 Hz, 2H), 3.27-3.08 (m, 4H), 2.38 (d, J=0.8 Hz, 3H), 1.74-1.67 (m, 2H), 1.66-1.63 (m, 9H), 1.51-1.49 (m, 2H), 1.47 (t, J=7.2 Hz, 3H), 1.08 (s, 6H); LCMS (ESI, M+1): 416.35.

Intermediate 6

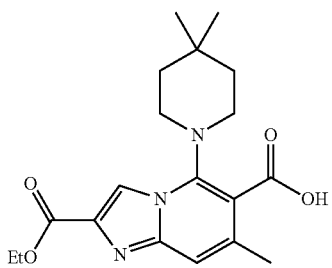

5-(4,4-Dimethylpiperidin-1-yl)-2-(ethoxycarbonyl)-7-methylimidazo[1,2-a]pyridine-6-carboxylic acid: A solution of 6-tert-butyl 2-ethyl 5-(4,4-dimethylpiperidin-1-yl)-7-methylimidazo[1,2-a]pyridine-2,6-dicarboxylate (0.61 g, 1.47 mmol) in TFA (15 mL) was stirred 2 h and then concentrated in vacuo. The residue was taken up in THF/benzene and concentrated in vacuo (×2) to remove residual TFA. To provide the product as a viscous brown oil (~1.2 g). This material was used directly. ¹H NMR (400 MHz, CDCl₃) δ 8.10 (s, 1H), 7.60 (s, 1H), 4.51 (q, J=7.0 Hz, 2H), 3.44-3.04 (m, 4H), 2.54 (s, 3H), 1.62 (br. s., 4H), 1.50-1.41 (m, 3H), 1.10 (s, 6H); LCMS (ESI, M+1):360.3.

Intermediate 7

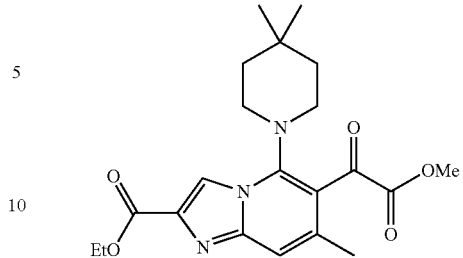

Ethyl 5-(4,4-dimethylpiperidin-1-yl)-6-(2-methoxy-2-oxoacetyl)-7-methylimidazo[1,2-a]pyridine-2-carboxylate: A solution of 5-(4,4-dimethylpiperidin-1-yl)-2-(ethoxycarbonyl)-7-methylimidazo[1,2-a]pyridine-6-carboxylic acid (~1.2 g, 1.47 mmol, 1 equiv) from previous reaction in DCM (15 mL) and DMF (0.02 mL) was added oxalyl chloride (0.31 mL, 3.53 mmol, 2.4 equiv). Gas evolution observed. After 1 h, reaction was concentrated in vacuo. The crude acid chloride was then taken up in DCM (15 mL). To this solution was added 1-(cyanomethyl)tetrahydro-1H-thiophen-1-ium, bromide salt (0.92 g, 4.41 mmol, 3 equiv) and DIPEA. After stirring 18 h, the reaction was added to saturated aqueous sodium bicarbonate solution and extracted with DCM (×3). The combined DCM extracts were dried (Na₂SO₄) and concentrated in vacuo. The crude sulfur ylide was then taken up in MeOH (15 mL) and water (1 mL). Oxone (1.45 g, 2.35 mmol, 1.6 equiv) was added. The white slurry was stirred 18 h. The reaction was added to saturated aqueous sodium bicarbonate solution and extracted with DCM (×3). The combined DCM extracts were dried (Na₂SO₄) and concentrated in vacuo. The crude product was purified via flash silica gel chromatography (10-100% EtOAc/hexane) to provide the product (0.28 g, 47%) as a yellow oil heavily contaminated (~50%) with the methyl ester of the starting acid, 6-methyl 2-ethyl 5-(4,4-dimethylpiperidin-1-yl)-7-methylimidazo[1,2-a]pyridine-2,6-dicarboxylate. Used as is in the subsequent reaction. LCMS (ESI, M+1): 402.1.

Intermediate 8

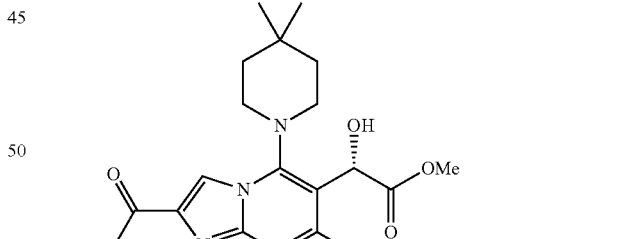

(S)-Ethyl 5-(4,4-dimethylpiperidin-1-yl)-6-(1-hydroxy-2-methoxy-2-oxoethyl)-7-methylimidazo[1,2-a]pyridine-2-carboxylate: To a solution of ethyl 5(4,4-dimethylpiperidin-1-yl)-6-(2-methoxy-2-oxoacetyl)-7-methylimidazo[1,2-a]pyridine-2-carboxylate (280 mg, 0.70 mmol, 1 equiv) in toluene (7 mL) was added R-5,5-diphenyl-2-methyl-3,4-propano-1,3,2-oxazaborlidine (309 mg, 1.12 mmol, 1.6 equiv). The reaction was then cooled to −30° C. (IPA/dry ice) and catecholborane (0.27 mL of a 50% solution in toluene, 1.12 mmol, 1.6 equiv) was added. After 3 h, the reaction was added to 10% aqueous potassium carbonate and extracted with EtOAc (×3). The combined EtOAc extracts were dried (Na₂SO₄) and concentrated in vacuo. The crude product was purified via flash silica gel chromatography (10-100% EtOAc/hexane) to provide the product (144 mg, 51%) contaminated with a small amount of residual CBS amino alcohol. Use as is. ¹H NMR (400 MHz, CDCl3) δ 8.25 (s, 1H), 7.37 (s, 1H), 5.62 (s, 1H), 4.48 (q, J=7.3 Hz, 2H), 3.80 (s, 3H), 3.09-2.90 (m, 4H), 2.40 (d, J=0.8 Hz, 3H), 1.75-1.61 (m, 4H), 1.46 (t, J=7.2 Hz, 3H), 1.14 (s, 3H), 1.09 (s, 3H); LCMS (ESI, M+1): 404.25.

Intermediate 9

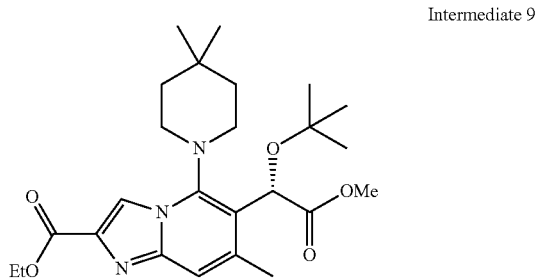 [SMILES: CCOC(=O)c1cn2c(N3CCC(C)(C)CC3)c([C@H](OC(C)(C)C)C(=O)OC)c(C)cc2n1]

(S)-Ethyl 6-(1-(tert-butoxy)-2-methoxy-2-oxoethyl)-5-(4,4-dimethylpiperidin-1-yl)-7-methylimidazo[1,2-a]pyridine-2-carboxylate: To a solution of (S)-ethyl 5-(4,4-dimethylpiperidin-1-yl)-6-(1-hydroxy-2-methoxy-2-oxoethyl)-7-methylimidazo[1,2-a]pyridine-2-carboxylate (144 mg, 0.36 mmol, 1 equiv) in tert-butyl acetate (7 mL) was added 70% perchloric acid (0.092 mL, 1.07 mmol, 3 equiv). An immediate white precipitate formed. DCM (5 mL) and more 70% perchloric acid (0.18 mL, 2.14 mmol, 6 equiv) was added. After 1 h, reaction was added cautiously to saturated aqueous sodium bicarbonate solution and extracted with EtOAc (×3). The combined EtOAc extracts were dried (Na₂SO₄) and concentrated in vacuo to provide the crude product. The crude product was purified via flash silica gel chromatography (10-100% EtOAc/hexane) to provide the product (47 mg, 29%) as a white foam. ¹H NMR (400 MHz, CDCl₃) δ 8.23 (s, 1H), 7.33-7.30 (m, 1H), 6.05-6.00 (m, 1H), 4.48 (d, J=7.3 Hz, 2H), 3.71 (s, 3H), 3.66-3.57 (m, 1H), 3.54-3.45 (m, 1H), 3.16-3.06 (m, 1H), 2.97-2.87 (m, 1H), 2.45 (d, J=1.0 Hz, 3H), 1.73-1.57 (m, 4H), 1.46 (t, J=7.0 Hz, 3H), 1.25 (s, 9H), 1.15 (s, 3H), 1.09 (s, 3H); LCMS (ESI, M+1): 460.3.

Intermediate 10

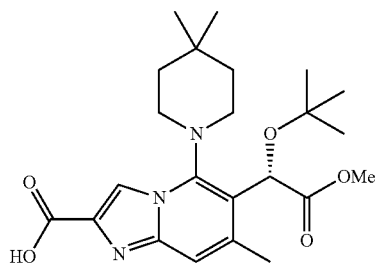

(S)-6-(1-(tert-Butoxy)-2-methoxy-2-oxoethyl)-5-(4,4-dimethylpiperidin-1-yl)-7-methylimidazo[1,2-a]pyridine-2-carboxylic acid sodium salt: To a solution of (S)-ethyl6-(1-(tert-butoxy)-2-methoxy-2-oxoethyl)-5-(4,4-dimethylpiperidin-1-yl)-7-methylimidazo[1,2-a]pyridine-2-carboxylate (47 mg, 0.102 mmol, 1 equiv) in dioxane (1.0 mL) was added 1 N NaOH (0.11 mL, 0.11 mmol, 1.1 equiv). After 18 h, the reaction was concentrated in vacuo to provide the crude product as a sodium salt. This material was used directly for the subsequent reaction. LCMS (ESI, M+1): 432.25.

EXAMPLE 1

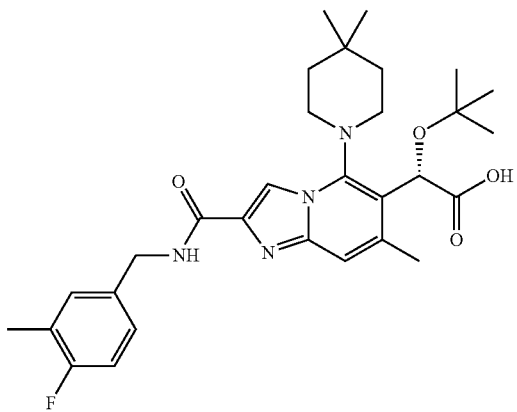 [SMILES: Cc1cc(CNC(=O)c2cn3c(N4CCC(C)(C)CC4)c([C@H](OC(C)(C)C)C(=O)O)c(C)cc3n2)ccc1F]

(S)-2-(tert-Butoxy)-2-(5-(4,4-dimethylpiperidin-1-yl)-2-((4-fluoro-3-methylbenzyl)carbamoyl)-7-methylimidazo[1,2-a]pyridin-6-yl)acetic acid: To a solution of (S)-6-(1-(tert-butoxy)-2-methoxy-2-oxoethyl)-5-(4,4-dimethylpiperidin-1-yl)-7-methylimidazo[1,2-a]pyridine-2-carboxylic acid, sodium salt (44 mg, 0.102 mmol, 1 equiv) and 4-fluoro-3-methylbenzylamine (43 mg, 0.306 mmol, 3 equiv) in DMF was added HATU (54 mg, 0.143 mmol, 1.4 equiv) giving a deep yellow solution. After 1.5 h, more HATU (54 mg, 0.143 mmol, 1.4 equiv) added. After stirring 1 h, water (0.5 mL) and lithium hydroxide monohydrate (86 mg, 2.04 mmol, 20 equiv) was added and reaction was heated to 60° C. After stirring 2 h, more lithium hydroxide monohydrate (86 mg, 2.04 mmol, 20 equiv) was added and reaction was heated to 90° C. After 1 h, the mixture was allowed to cool to ambient temperature and filtered. This solution was purified via preparative LC/MS with the following conditions: Column: Waters XBridge C18, 19×200 mm, 5-μm particles; Mobile Phase A: water with 20-mM ammonium acetate; Mobile Phase B: 95:5 acetonitrile:water with 20-mM ammonium acetate; Gradient: 35-75% B over 20 minutes, then a 5-minute hold at 100% B; Flow: 20 mL/min. Fractions containing the desired product were combined and dried via centrifugal evaporation to provide the product (35.6 mg, 65%).¹H NMR (500 MHz, DMSO-d₆) δ 8.94 (t, J=6.0 Hz, 1H), 8.11 (s, 1H), 7.27-7.22 (m, 2H), 7.18 (br. s., 1H), 7.07 (t, J=9.2 Hz, 1H), 5.78 (br. s., 1H), 4.42 (d, J=6.1 Hz, 2H), 3.54 (br. s., 2H), 3.24-3.16 (m, J=12.8 Hz, 2H), 2.41 (s, 3H), 2.21 (s, 3H), 1.60 (dd, J=18.9, 9.2 Hz, 2H), 1.51 (d, J=11.3 Hz, 1H), 1.43 (d, J=13.1 Hz, 1H), 1.18 (s, 9H), 1.12 (s, 3H), 1.04 (s, 3H); LCMS (ESI): 538.30.

Intermediate 11

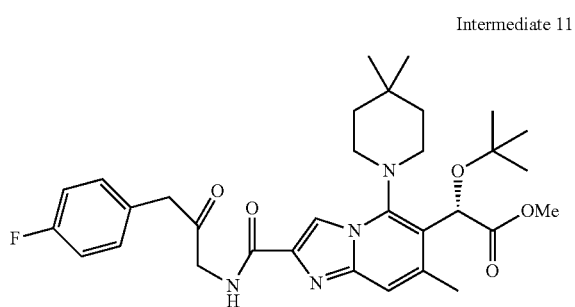 [SMILES: COC(=O)[C@@H](OC(C)(C)C)c1c(C)cc2nc(C(=O)NCC(=O)Cc3ccc(F)cc3)cn2c1N1CCC(C)(C)CC1]

(S)-Methyl 2-(tert-butoxy)-2-(5-(4,4-dimethylpiperidin-1-yl)-2-((3-(4-fluorophenyl)-2-oxopropyl)carbamoyl)-7-methylimidazo[1,2-a]pyridin-6-yl)acetate: To a solution of (S)-6-(1-(tert-butoxy)-2-methoxy-2-oxoethyl)-5-(4,4-dimethylpiperidin-1-yl)-7-methylimidazo[1,2-a]pyridine-2-carboxylic acid (29 mg, 0.067 mmol, 1 equiv) in DCM (1.5 mL) was added (COCl)$_2$ (0.040 mL, 0.081 mmol, 1.2 equiv) and DMF (one drop) and the reaction was stirred at room temp for 1 h. The reaction was concentrated in vacuo and the crude acid chloride was then added to a pre-stirred solution of 1-amino-3-(4-fluorophenyl)propan-2-one, HCl (27.4 mg, 0.134 mmol, 2 equiv) and DIPEA (0.070 mL, 0.403 mmol, 6 equiv) in DCM (2 mL). The resulting solution was stirred at room temperature for 2 h. Water was then added and the mixture was extracted with DCM, dried (Na$_2$SO$_4$), and concentrated in vacuo. The crude was purified by flash column chromatography (5-70% EtOAc/hexane) to afford (S)-methyl 2-(tert-butoxy)-2-(5-(4,4-dimethylpiperidin-1-yl)-2-((3(4-fluorophenyl)-2-oxopropyl)carbamoyl)-7-methylimidazo[1,2-a]pyridin-6-yl)acetate (20 mg, 50%) as light yellow solid. $^1$H NMR (500 MHz, CDCl$_3$) δ 7.77-7.71 (m, 1H), 7.26-7.22 (m, 2H), 7.12-7.03 (m, 3H), 6.25 (br. s., 0.7H), 5.89 (s, 0.3H), 5.53 (s, 0.7H), 5.45 (s, 0.3H), 4.47-4.33 (m, 2H), 4.27-4.19 (m, 2H), 3.81 (s, 2H), 2.76 (s, 1H), 2.69 (s, 2H), 2.20-2.12 (m, 1H), 2.10-1.98 (m, 2H), 1.79-1.68 (m, 1H), 1.60-1.54 (m, 2H), 1.28 (t, J=7.1 Hz, 3H), 1.26 (s, 4H), 1.25 (br. s., 2H), 1.23 (s, 7H), 1.14 (s, 2H). LCMS (ESI, M+1): 593.4.

EXAMPLE 2

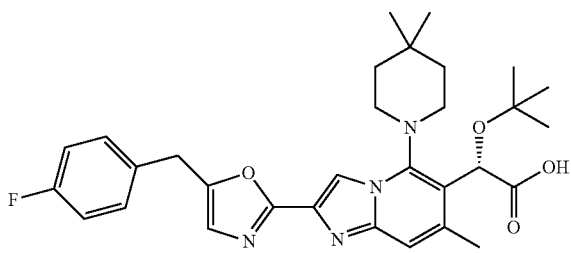 [SMILES: Cc1cc2nc(-c3ncc(Cc4ccc(F)cc4)o3)cn2c(N2CCC(C)(C)CC2)c1[C@H](OC(C)(C)C)C(=O)O]

(S)-2-(tert-Butoxy)-2-(5-(4,4-dimethylpiperidin-1-yl)-2-(5-(4-fluorobenzyl)oxazol-2-yl)-7-methylimidazo[1,2-a]pyridin-6-yl)acetic acid: (S)-methyl 2-(tert-butoxy)-2-(5-(4,4-dimethylpiperidin-1-yl)-2-((3-(4-fluorophenyl)-2-oxopropyl)carbamoyl)-7-methylimidazo[1,2-a]pyridin-6-yl)acetate (45 mg, 0.077 mmol, 1 equiv) was stirred with Burgess reagent (55.4 mg, 0.232 mmol, 3 equiv) in THF (0.39 mL) at 80° C. for 1 h. Upon completion, MeOH (0.6 mL), water (0.2 ml), and LiOH (50 mg) was added. The reaction was stirred at 60° C. for 2 h. Upon completion, the reaction was allowed to cool to ambient temperature, filtered, and purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 15 minutes, then a 5-minute hold at 100% B; Flow: 20 mL/min to provide the product (15.9 mg, 37%). $^1$H NMR (500 MHz, DMSO-d$_6$) δ 8.15 (s, 1H), 7.39-7.32 (m, 2H), 7.24 (s, 1H), 7.17 (t, J=8.4 Hz, 2H), 7.02 (s, 1H), 5.74 (br. s., 1H), 4.13 (s, 2H), 3.53 (br. s., 1H), 3.42 (d, J=10.1 Hz, 1H), 3.21 (d, J=11.3 Hz, 1H), 2.93-2.85 (m, 1H), 2.39 (s, 3H), 1.69-1.36 (m, 4H), 1.16 (s, 9H), 1.10 (s, 3H), 1.02 (s, 3H); LCMS (ESI, M): 548.3.

EXAMPLE 3

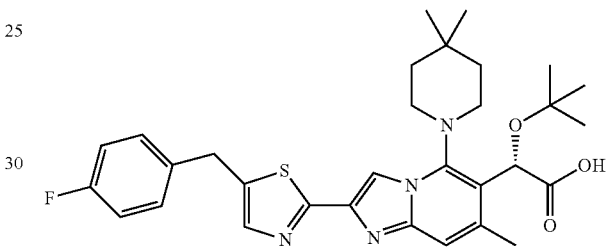

(S)-2-(tert-Butoxy)-2-(5-(4,4-dimethylpiperidin-1-yl)-2-(5-(4-fluorobenzyl)thiazol-2-yl)-7-methylimidazo[1,2-a]pyridin-6-yl)acetic acid: To a solution of (S)-methyl 2-(tert-butoxy)-2-(5-(4,4-dimethylpiperidin-1-yl)-((3-(4-fluorophenyl)-2-oxopropyl)carbamoyl)-7-methylimidazo[1,2-a]pyridin-6-yl)acetate (30 mg, 0.052 mmol, 1 equiv) in toluene (1 mL) was added Lawesson's reagent (23 mg, 0.057 mmol, 1.1 equiv). The reaction was heated at 60° C. for 2 h. Upon cooling to ambient temperature, the reaction was concentrated in vacuo. The crude product was taken up in MeOH (1 mL) and 1 N NaOH (0.16 mL, 0.16 mmol, 3 equiv) was added. The reaction was stirred at 65° C. for 4 h. Upon completion, the reaction was allowed to cool to ambient temperature, filtered, and purified via preparative LC/MS with the following conditions: Column: XBridge C18, 19×mm, 5-μm particles; Mobile Phase A: 5:95 acetonitrile: water with 10-mM ammonium acetate; Mobile Phase B: 95:5 acetonitrile: water with 10-mM ammonium acetate; Gradient: 40-100% B over 20 minutes, then a 5-minute hold at 100% B; Flow: 20 mL/min to provide the product (6.2 mg, 21%). $^1$H NMR (500 MHz, DMSO-d$_6$) δ 8.11 (s, 1H), 7.67 (s, 1H), 7.35 (dd, J=8.2, 5.8 Hz, 2H), 7.23 (s, 1H), 7.16 (t, J=8.9 Hz, 2H), 5.75 (br. s., 1H), 4.22 (s, 2H), 3.30-3.29 (m, 4H), 2.38 (s, 3H), 1.90 (s, 5H), 1.17 (s, 9H), 1.12 (s, 3H), 1.03 (s, 3H). LCMS (ESI, M+1)=565.3.

EXAMPLE 4

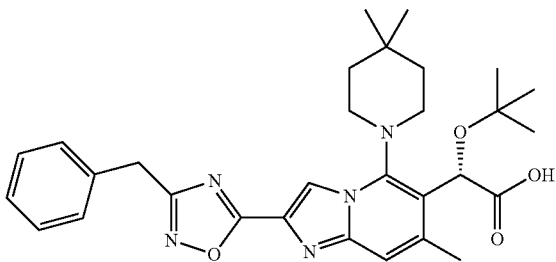 [SMILES: Cc1cc2nc(-c3nc(Cc4ccccc4)no3)cn2c(N2CCC(C)(C)CC2)c1[C@H](OC(C)(C)C)C(=O)O]

(S)-2-(2-(3-Benzyl-1,2,4-oxadiazol-5-yl)-5-(4,4-dimethylpiperidin-1yl)-7-methylimidazo[1,2-a]pyridin-6-yl)-2-(tert-butoxy)acetic acid: To a solution of (S)-6-(1-(tert-butoxy)-2-methoxy-2-oxoethyl)-5-(4,4-dimethylpiperidin-1-yl)-7-methylimidazo[1,2-a]pyridine-2-carboxylic acid sodium salt (20 mg, 0.044 mmol, 1 equiv) in DCM (0.4 mL) was added oxalyl chloride (0.006 mL, 0.066 mmol, 1.5 equiv) and DMF (one drop). The reaction was stirred for 1 h and then concentrated in vacuo. The residue was redissolved in MeCN (0.4 mL) and (Z)-N'-hydroxy-2-phenylacetimidamide (7 mg, 0.049 mmol, 1.1 equiv) and DIPEA (0.010 mL, 0.057 mmol, 1.3 equiv) was added. The reaction was then heated to 85° C. for 18 h. Upon cooling to ambient temperature, the reaction was concentrated in vacuo. The crude product was taken up in MeOH (1 mL), water (0.1 ml), and LiOH (79 mg, 3.30 mmol, 60 equiv) was added. The reaction was stirred at 60° C. for 1 h. Upon completion, the reaction was allowed to cool to ambient temperature, filtered, and purified via preparative LC/MS with the following conditions: Column: XBridge C18, 19×mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 20 minutes, then a 5-minute hold at 100% B; Flow: 20 mL/min to provide the product (10.3 mg, 33%). $^1$H NMR (500 MHz, DMSO-$d_6$) δ 8.51 (s, 1H), 7.35 (d, J=4.0 Hz, 5H), 7.27 (d, J=4.3 Hz, 1H), 5.78 (br. s., 1H), 4.17 (s, 2H), 2.88 (s, 2H), 2.40 (s, 3H), 1.66-1.37 (m, 4H), 1.16 (s, 9H), 1.11 (s, 3H), 1.01 (s, 3H); LCMS (ESI, M): 531.3.

EXAMPLE 5

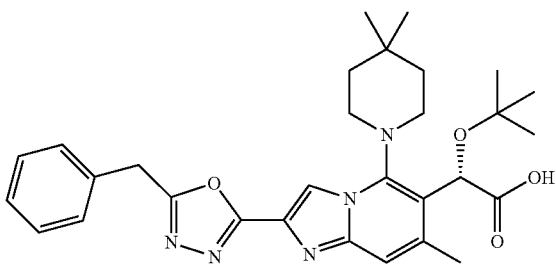 [SMILES: Cc1cc2nc(-c3nnc(Cc4ccccc4)o3)cn2c(N2CCC(C)(C)CC2)c1[C@H](OC(C)(C)C)C(=O)O]

(S)-2-(2-(5-Benzyl-1,3,4-oxadiazol-2-yl)-5-(4,4-dimethylpiperidin-1-yl)-7-methylimidazo[1,2-a]pyridin-6-yl)-2-(tert-butoxy)acetic acid: To a solution of (S)-6-(1-(tert-butoxy)-2-methoxy-2-oxoethyl)-5-(4,4-dimethylpiperidin-1-yl)-7-methylimidazo[1,2-a]pyridine-2-carboxylic acid sodium salt (30 mg, 0.070 mmol, 1 equiv) in DCM (0.5 mL) was added oxalyl chloride (11 mg, 0.083 mmol, 1.2 equiv) and DMF (one drop). The reaction was stirred for 1 h and then concentrated in vacuo. The residue was redissolved in DCM (0.70 mL) and 2-phenylacetohydrazide (15 mg, 0.097 mmol, 1.4 equiv) and DIPEA (0.027 mL, 0.153 mmol, 2.2 equiv) was added. After stirring 30 min, Burgess reagent (66 mg, 0.278 mmol, 4 equiv) was added and the reaction was stirred 18 h. The reaction was concentrated in vacuo. The crude product was taken up in MeOH (1 mL), water (0.1 ml), and LiOH (83 mg, 3.48 mmol, 50 equiv) was added. The reaction was stirred at 60° C. for 1 h. Upon completion, the reaction was allowed to cool to ambient temperature, filtered, and purified via preparative LC/MS with the following conditions: Column: XBridge C18, 19×mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 20 minutes, then a 5-minute hold at 100% B; Flow: 20 mL/min to provide the product (5 mg, 14%). $^1$H NMR (500 MHz, DMSO-$d_6$) δ 8.39 (s, 1H), 7.41-7.22 (m, 6H), 5.76 (br. s., 1H), 4.37 (s, 2H), 3.19 (d, J=11.6 Hz, 3H), 2.96-2.91 (m, 1H), 2.40 (s, 3H), 1.65-1.40 (m, 4H), 1.16 (s, 9H), 1.12 (br. s., 3H), 1.02 (br. s., 3H); LCMS (ESI, M): 531.3.

Intermediate 12

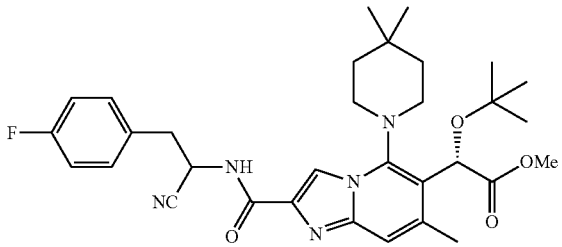

(2S)-Methyl 2-(tert-butoxy)-2-(2-((1-cyano-2-(4-fluorophenyl)ethyl)carbamoyl)-5-(4,4-dimethylpiperidin-1-yl)-7-methylimidazo[1,2-a]pyridin-6-yl)acetate: A solution of (S)-6-(1-(tert-butoxy)-2-methoxy-2-oxoethyl)-5-(4,4-dimethylpiperidin-1-yl)-7-methylimidazo [1,2-a]pyridine-2-carboxylic acid sodium salt (110 mg, 0.242 mmol, 1 equiv), 2-amino-3-(4-fluorophenyl)propanenitrile, HCl (68 mg, 0.339 mmol, 1.4 equiv), DIPEA (0.13 mL, 0.339 mmol, 3 equiv), and HATU (129 mg, 0.339 mmol, 1.4 equiv) in DMF (1.4 mL) was stirred 1 h. The reaction was then diluted with EtOAc, washed with water, dried (Na$_2$SO$_4$), and concentrated in vacuo. The crude product was purified by flash column chromatography (0-100% EtOAc [2% TEA]/ hexane) to provide the product (112 mg, 80%) as a white solid. $^1$H NMR (400 MHz, CDCl$_3$) δ 8.23-8.16 (m, 1H), 7.75-7.67 (m, 1H), 7.36-7.29 (m, 2H), 7.22-7.17 (m, 1H), 7.11-7.03 (m, 2H), 6.08-6.00 (m, 1H), 5.38-5.28 (m, 1H), 3.71(d, J=1.3 Hz, 3H), 3.63-3.56 (m, 1H), 3.52-3.43 (m, 1H), 3.27-3.18 (m, 2H), 3.13-3.04 (m, 1H), 2.95-2.84 (m, 1H), 2.46 (s, 3H), 1.74-1.62 (m, 2H), 1.54-1.43 (m, 2H), 1.25 (s, 9H), 1.14 (s, 3H), 1.08 (s, 3H); LCMS (ESI, M+1): 578.35.

Intermediate 13

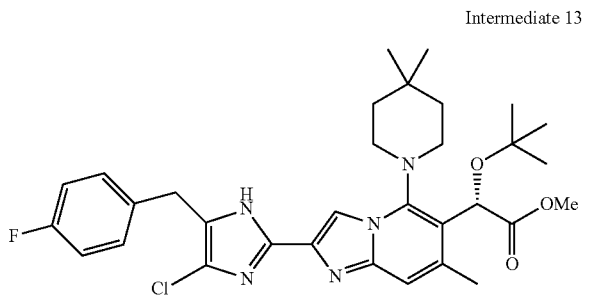 [SMILES: COC(=O)[C@@H](OC(C)(C)C)c1c(C)cc2nc(-c3nc(Cl)c(Cc4ccc(F)cc4)[nH]3)cn2c1N1CCC(C)(C)CC1]

(S)-Methyl2-(tert-butoxy)-2-(2-(4-chloro-5-(4-fluorobenzyl)-1H-imidazol-2-yl)-5-(4,4-dimethylpiperidin-1-yl)-7-methylimidazo[1,2-a]pyridin-6-yl)acetate: To a solution of (2S)-methyl 2-(tert-butoxy)-2-(2-((1-cyano-2-(4-fluorophenyl)ethyl)carbamoyl)-5-(4,4-dimethylpiperidin-1-yl)-7-methylimidazo[1,2-a]pyridin-6-yl)acetate (101 mg, 0.175 mmol, 1 equiv) and CCl$_4$ (0.042, 0.437 mmol, 2.5 equiv) in MeCN (1.7 mL) was added PPh$_3$ (115 mg, 0.437 mmol, 2.5 equiv). The reaction was heated to 45° C. for 6 h. Upon cooling to ambient temperature, the reaction was diluted with DCM, washed with 1 N NaOH, dried (Na$_2$SO$_4$), and concentrated in vacuo. The crude product was purified by flash column chromatography (0-100% EtOAc [2% TEA]/hexane) to provide the product (60 mg, 58%) as a yellow solid. $^1$H NMR (400 MHz, CDCl$_3$) δ 8.11-8.03 (m, 1H), 7.27-7.22 (m, 3H), 7.03-6.95 (m, 2H), 6.02-5.90 (m, 1H), 4.00 (s, 2H), 3.73 (s, 3H), 3.63-3.54 (m, 1H), 3.49-3.40 (m, 1H), 3.20-3.10 (m, 1H), 3.02-2.92 (m, 1H), 2.48 (br. s., 3H), 1.78-1.51 (m, 4H), 1.24 (s, 9H), 1.16 (s, 3H), 1.09 (s, 3H); LCMS (ESI, M+1): 596.35.

EXAMPLE 6

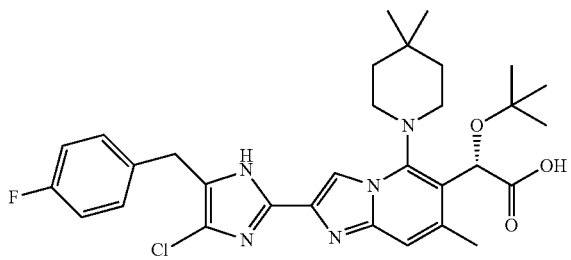 [SMILES: Cc1cc2nc(-c3nc(Cl)c(Cc4ccc(F)cc4)[nH]3)cn2c(N2CCC(C)(C)CC2)c1[C@H](OC(C)(C)C)C(=O)O]

(S)-2-(tert-Butoxy)-2-(2-(4-chloro-5-(4-fluorobenzyl)-1H-imidazol-2-yl)-5-(4,4-dimethylpiperidin-1-yl)-7-methylimidazo[1,2-a]pyridin-6)acetic acid: A solution of (S)-methyl 2-(tert-butoxy)-2-(2-(4-chloro-5-(4-fluorobenzyl)-1H-imidazol-2-yl)-5-(4,4-dimethylpiperidin-1-yl)-7-methylimidazo[1,2-a]pyridin-6-yl)acetate(20 mg, 0.034 mmol, 1 equiv) and LiOH monohydrate (42 mg, 1.01 mmol, 30 equiv) in MeOH (1 mL) and water (a few drops) was heated at 60° C. for 3 h. Upon cooling to ambient temperature, the reaction was filtered and purified by preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 40-80% B over 15 minutes, then a 5-minute hold at 100% B; Flow: 20 mL/min to provide the product (14.8 mg, 76%).$^1$H NMR (500 MHz, DMSO-d$_6$) δ 13.21-12.87 (m, 1H), 8.03 (s, 1H), 7.33-7.28 (m, 2H), 7.22 (s, 1H), 7.14 (t, J=8.9 Hz, 2H), 5.80 (br. s., 1H), 3.92 (s, 2H), 3.62-3.54 (m, 2H), 3.23-3.14 (m, J=9.5 Hz, 2H), 2.40 (s, 3H), 1.67-1.55 (m, 2H), 1.50 (d, J=12.5 Hz, 1H), 1.43 (d, J=12.5 Hz, 1H), 1.17 (s, 9H), 1.13 (s, 3H), 1.03 (s, 3H); LCMS (ESI, M+1): 582.3.

EXAMPLE 7

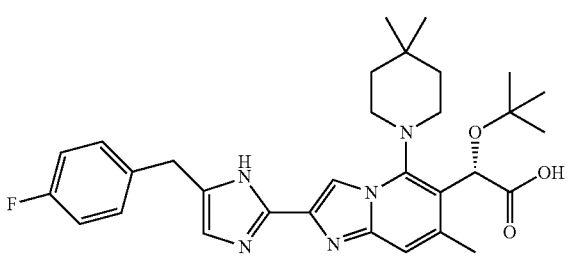 [SMILES: Cc1cc2nc(-c3ncc(Cc4ccc(F)cc4)[nH]3)cn2c(N2CCC(C)(C)CC2)c1[C@H](OC(C)(C)C)C(=O)O]

(S)-2-(tert-Butoxy)-2-(5-(4,4-dimethylpiperidin-1-yl)-2-(5-(4-fluorobenzyl)-1H-imidazol-2-yl)-7-methylimidazo[1,2-a]pyridin-6-yl)acetic acid: A solution of (S)-methyl 2-(tert-butoxy)-2-(2-(4-chloro-5-(4-fluorobenzyl)-1H-imidazol-2-yl)-5-(4,4-dimethylpiperidin-1-yl)-7-methylimidazo[1,2-a]pyridin-6-yl)acetate (40 mg, 0.067 mmol, 1 equiv), TsOH monohydrate (15 mg, 0.081 mmol, 1.2 equiv), and 10% Pd/C (14 mg, 0.013 mmol, 0.2 equiv) in MeOH (1.3 mL) was stirred under a balloon of hydrogen for 6 d. The reaction was filtered through Celite eluting with MeOH. The filtrate was concentrated in vacuo. The crude imidazole was taken up in MeOH (1 mL) and water (several drops). LiOH monohydrate (84 mg, 2.01 mmol, 30 equiv) was added and the reaction was heated at 60° C. for 2 h. Upon cooling to ambient temperature, the reaction was filtered and purified by preparative LC/MS with the following conditions: Column: XBridge C18, 19×mm, 5-μm particles; Mobile Phase A: 5:95 acetonitrile: water with 10-mM ammonium acetate; Mobile Phase B: 95:5 acetonitrile: water with 10-mM ammonium acetate; Gradient: 40-100% B over 20 minutes, then a 5-minute hold at 100% B; Flow: 20 mL/min to provide the product (4.4 mg, 11%). $^1$H NMR (500 MHz, DMSO-d$_6$) δ 8.03-7.91 (m, 1H), 7.38-7.28 (m, 2H), 7.16-7.04 (m, 3H), 6.79-6.70 (m, 1H), 5.62-5.43 (m, 1H), 3.89-3.84 (m, 2H), 3.67-3.52 (m, 4H), 2.40 (s, 3H), 1.63-1.34 (m, 4H), 1.14 (s, 9H), 1.12 (br. s., 3H), 1.03 (s, 3H); LCMS (ESI, M+1): 548.4.

Intermediate 14

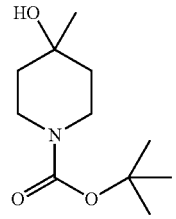

tert-Butyl 4-hydroxy-4-methylpiperidine-1-carboxylate: Under an N2 atmosphere, a 3N solution in ether of methylmagnesium bromide (1.67 mL, 5.02 mmol) was added dropwise to a cooled (−25° C.) solution of tert-butyl 4-hydroxy-4-methylpiperidine-1-carboxylate (4 g, 20.08 mmol) in ether (20 mL). The reaction mixture was allowed to warm to rt and was stirred for 2 h. It was then cooled to 0° C. and quenched by the addition of sat. aq. ammonium chloride. Another 20 mL of ether was added and the mixture was partitioned in a separatory funnel. The organic phase was set aside and the aqueous phase was extracted with another 20 mL of ether. The combined ether extracts were dried over MgSO₄, filtered and evaporated to obtain an oil, which was then purified by biotage, eluting with 0-50% EtOAc/hexane to obtain tert-butyl 4-hydroxy-4-methylpiperidine-1-carboxylate (4.30 g, 18.0 mmol, 90%) as a colorless oil. $^1$H NMR (400MHz, CDCl₃) δ 3.84-3.65 (m, 2H), 3.34-3.18 (m, 2H), 2.59-2.39 (m, 1H), 1.61-1.53 (m, 4H), 1.50-1.45 (m, 9H), 1.32-1.27 (m, 3H).

Intermediate 15

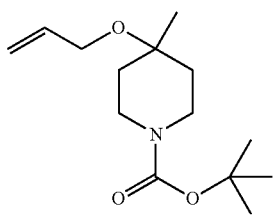

tert-Butyl 4-(allyloxy)-4-methylpiperidine-1-carboxylate: To a mixture of tert-butyl4-hydroxy-4-methylpiperidine-1-carboxylate (4.30 g, 20.0 mmol) in DMF (50 mL) at 0° C. was added NaH (60 wt %) (1.60 g, 39.9 mmol). The mixture was then stirred at rt for 2 h. At this time allyl bromide (8.64 mL, 100 mmol) was added slowly over the course of 5 min. The reaction mixture was stirred at rt for 3 h. It was then cooled to 0° C. and quenched with sat. aq. ammonium chloride. The reaction mixture was extracted with ether. The organic phase was dried over MgSO₄, filtered and concentrated to obtain a colorless oil, which was then purified by biotage, eluting with 0-25% EtOAc/hexane to isolate 3.1 g (61%) of tert-butyl 4-(allyloxy)-4-methylpiperidine-1-carboxylate as a colorless oil. $^1$H NMR (500 MHz, CDCl₃) δ 6.02-5.90 (m, 1H), 5.32 (dd, J=17.2, 1.7 Hz, 1H), 5.16 (dd, J=10.4, 1.4 Hz, 1H), 3.94-3.88 (m, 2H), 3.73 (br. s., 2H), 3.19 (br. s., 2H), 1.78 (d, J=13.1 Hz, 2H), 1.53-1.42 (m, 11H), 1.21 (s, 3H).

Intermediate 16

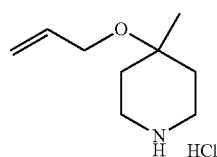

4-(Allyloxy)-4-methylpiperidine hydrogen chloride salt: A mixture of tert-butyl4-(allyloxy)-4-methylpiperidine-1-carboxylate (3.10 g, 12.1 mmol) and 4N HCl/dioxane (15 mL, 60.0 mmol) was stirred at rt for 3 h. It was then concentrated in vacuum to obtain 2.2 g (95%) of 4-(allyloxy)-4-methylpiperidine hydrochloride as a light brown solid. $^1$H NMR (500 MHz, CD₃OD) δ 6.02-5.92 (m, 1H), 5.33 (dd, J=17.2, 1.7 Hz, 1H), 5.15 (dd, J=10.6, 1.7 Hz, 1H), 3.96 (dt, J=5.1, 1.6 Hz, 2H), 3.23-3.18 (m, 4H), 2.06 (dd, J=15.3, 2.5 Hz, 2H), 1.77-1.69 (m, 2H), 1.31-1.28 (s, 3H). Free base (brown solid) is obtained by stirring HCl salt with aq Na₂CO₃ and extracting with DCM.

Intermediate 17

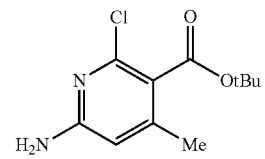

tert-butyl 6-amino-2-chloro-4-methylnicotinate. tert-butyl 2,6-dichloro-4-methylnicotinate (10.5 g, 40.1 mmol, 1 equiv), Pd₂(dba)₃ (1.84 g, 2.01 mmol, 0.05 equiv), xantphos (2.32 g, 4.01 mmol, 0.1 equiv), and Cs₂CO₃ slurried in dioxane (deoxygenated by bubbling nitrogen through it for 10 min) added. Benzophenone imine (8.0 mL, 48.1 mmol, 1.2 equiv) added and the mixture was heated at 90° C. for 1 h. Upon cooling to ambient temperature, the reaction was diluted with EtOAc and washed with water, dried (Na₂SO₄), and concentrated in vacuo. The crude product was taken up in MeOH (200 mL) and NaOAc (9.87, 120 mmol, equiv) and hydroxlamine hydrochloride (5.57 g, 80 mmol, 2 equiv) was added. After 30 min, the reaction was added to 1 N NaOH and extracted with DCM (×2). The combined DCM extracts were dried (Na₂SO₄) and concentrated in vacuo. The crude product was purified by flash column chromatography (0-30% EtOAc/hex) to afford tert-butyl6-amino-2-chloro-4-methylnicotinate (7.5 g, 77%). $^1$H NMR (400 MHz, CDCl₃) δ 6.22 (d, J=0.8 Hz, 1H), 4.58 (br. s., 2H), 2.27 (d, J=0.8 Hz, 3H), 1.60 (s, 9H); LCMS (ESI, M+1): 243.1.

Intermediate 18

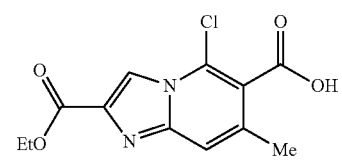

6-tert-butyl 2-ethyl 5-chloro-7-methylimidazo[1,2-a]pyridine-2,6-dicarboxylate. A solution of tert-butyl 6-amino-2-chloro-4-methylnicotinate (9.4 g, 38.7 mmol, 1 equiv) and ethyl bromopyruvate (6.5 mL, 46.5 mmol, 1.2 equiv) in EtOH (194 mL) was heated to reflux for 2 h. Upon cooling to ambient temperature, the solution was concentrated in vacuo. The residue was triturated in ether and filtered to provide the product (11.4 g, 70%) as a cream colored solid. LCMS (ESI, M+1): 339.1.

Intermediate 19

5-chloro-2-(ethoxycarbonyl)-7-methylimidazo[1,2-a]pyridine-6-carboxylic acid. 6-tert-butyl2-ethyl5-chloro-7-methylimidazo[1,2-a]pyridine-2,6-dicarboxylate (11.4 g, 27.2 mmol, 1 equiv) was treated with TFA (100 mL) and stirred for 2 h. Upon completion, the reaction was concentrated in vacuo. The crude product was triturated in ether and filtered to provide the product (10.8 g, 100%) as a cream colored solid. LCMS (ESI, M+1): 283.1.

Intermediate 20

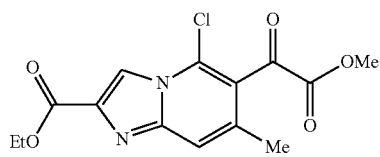

ethyl 5-chloro-6-(2-methoxy-2-oxoacetyl)-7-methylimidazo[1,2-a]pyridine-2-carboxylate. To a slurry of 5-chloro-2-(ethoxycarbonyl)-7-methylimidazo[1,2-a]pyridine-6-carboxylic acid (0.46 g, 1.623, 1 equiv) and 1-(cyanomethyl)tetrahydro-1H-thiophen-1-ium, bromide salt (0.47 g, 2.27 mmol, 1.4 equiv) in DCM (16 mL) was added DIPEA (1.13 mL, 6.49 mmol, 4 equiv) then HATU (0.86 g, 2.27 mmol, 1.4 equiv). After 2 h, more 1-(cyanomethyl)tetrahydro-1H-thiophen-1-ium, bromide salt (0.20 g) and DIPEA (0.5 mL) added. After stirring 18 h, the reaction was added to saturated aqueous NaHCO$_3$ and extracted with DCM (×2). The combined DCM extracts were dried (Na$_2$SO$_4$) and concentrated in vacuo. The crude sulfur ylide was taken up in MeOH (16 mL) and a solution of Oxone (2.4 g, 3.90 mmol, 2.4 equiv) in water (5 mL) was added. After 2 d, more Oxone (2.4 g, 3.90 mmol, 2.4 equiv) was added. After 6 h, the reaction was added cautiously to saturated aqueous NaHCO$_3$ and extracted with DCM (×3). The combined DCM extracts were dried (Na$_2$SO$_4$) and concentrated in vacuo. The crude product was purified by flash column chromatography (20-100% EtOAc/hex) to provide the product (0.40, 76%) as a viscous yellow oil. $^1$H NMR (500 MHz, CDCl$_3$) δ 8.37 (d, J=0.8 Hz, 1H), 7.55-7.52 (m, 1H), 4.51 (q, J=7.2 Hz, 2H), 4.01 (s, 3H), 2.40 (d, J=1.1 Hz, 3H), 1.47 (t, J=7.2 Hz, 3H); LCMS (ESI, M+1): 325.05.

Intermediate 21

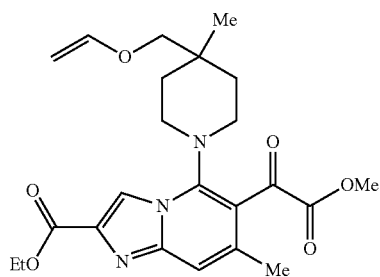

Ethyl 5-(4-(allyloxy)-4-methylpiperidin-1-yl)-6-(2-methoxy-2-oxoacetyl)-7-methylimidazo[1,2-a]pyridine-2-carboxylate: A solution of ethyl 5-chloro-6-(2-methoxy-2-oxoacetyl)-7-methylimidazo[1,2-a]pyridine-2-carboxylate (0.75 g, 2.31 mmol, 1 equiv), 4-allyloxy-4-methylpiperidine, HCl (0.66 g, 3.46 mmol, 1.5 equiv), and DIPEA (1.21 mL, 6.93 mmol, 3 equiv) in DMF (11.5 mL) was stirred for 1 h. The reaction was then added to saturated aqueous NaHCO$_3$ and extracted with EtOAc (×2). The combined EtOAc extracts were dried (Na$_2$SO$_4$) and concentrated in vacuo. The crude product was purified via silica gel flash chromatography (0-100% EtOAc [2% TEA]/hexane) to provide the product (0.85 g, 83%). LCMS (ESI, M+1): 444.25.

Intermediate 22

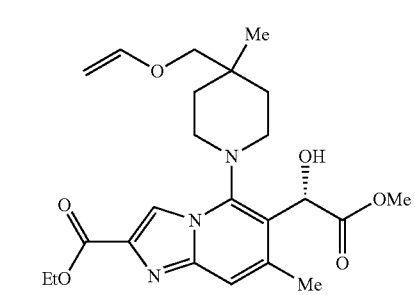

(S)-Ethyl 5-(4-(allyloxy)-4-methylpiperidin-1-yl)-6-(1-hydroxy-2-methoxy-2-oxoethyl)-7-methylimidazo[1,2-a]pyridine-2-carboxylate: To a stirred yellow solution of ethyl 5-(4-(allyloxy)-4-methylpiperidin-1-yl)-6-(2-methoxy-2-oxoacetyl)-7-methylimidazo[1,2-a]pyridine-2-carboxylate (0.86 g, 1.94 mmol, 1 equiv) in toluene (19 mL) was added (R)-1-methyl-3,3-diphenylhexahydropyrrolo[1,2-c][1,3,2]oxazaborole/toluene (0.54 g, 1.94 mmol, 1 equiv). The reaction was cooled to −40° C. (acetonitrile/dry ice bath) and a solution of 50% catechoborane in toluene (0.93 mL, 3.88 mmol, 2 equiv) was added over 10 min. The reaction mixture was stirred at −15° C. for 2 h. Upon completion, the reaction was diluted with EtOAc (30 mL) and sat. NaHCO$_3$ (10 mL). The mixture was stirred vigorously for 30 min. The organic phase was washed with saturated aqueous NaHCO$_3$ (2×5 mL), dried (Na$_2$SO$_4$), and concentrated in vacuo. The crude product was purified by silica gel chromatography (0-10% MeOH/DCM) to afford desired product (0.86 g, 100%) as an off-white solid. LCMS (ESI, M+1): 446.25.

Intermediate 23

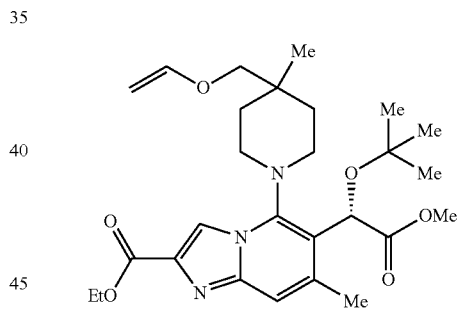

(S)-Ethyl 5-(4-(allyloxy)-4-methylpiperidin-1-yl)-6-(1-(tert-butoxy)-2-methoxy-2-oxoethyl)-7-methylimidazo[1,2-a]pyridine-2-carboxylate: (S)-Ethyl 5-(4,4-dimethylpiperidin-1-yl)-6-(1-hydroxy-2-methoxy-2-oxoethyl)-7-methylimidazo[1,2-a]pyridine-2-carboxylate (1.3 g, 3.22 mmol, 1 equiv) was suspended in DCM (3 mL) and tert-Butyl acetate (10 mL). To this mixture was added 70% HClO$_4$ (0.831 mL, 9.67 mmol, 3 equiv) through sealed rubber stopper. After 2 h, LCMS indicated about 60% conversion. The reaction was washed with 1 N NaOH, dried (Na$_2$SO$_4$), and concentrated in vacuo. The crude product was purified via silica gel flash chromatography (0-100% EtOAc [2% TEA]/hexane) to provide the product (0.68 g, 46%). $^1$H NMR (400 MHz, CDCl$_3$) 8.22 (d, J=0.8 Hz, 1H), 7.31 (s, 1H), 6.02 (s, 1H), 4.47 (q, J =7.2 Hz, 2H), 3.70 (s, 3H), 3.60 (td, J=11.4, 2.8 Hz, 1H), 3.49 (td, J=11.5, 2.6 Hz, 1H), 3.10 (dt, J=11.9, 3.5 Hz, 1H), 2.95-2.86 (m, 1H), 2.44 (d, J=1.0 Hz, 3H), 1.73-1.48 (m, 7H), 1.45 (t, J=7.0 Hz, 4H), 1.24 (s, 10H), 1.15 (s, 3H), 1.08 (s, 3H); LCMS (ESI, M+1): 502.35.

Intermediate 24

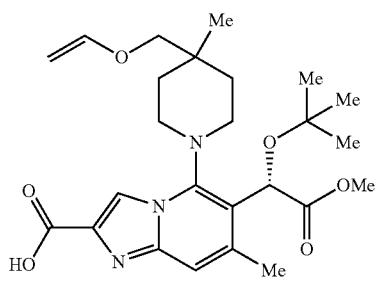

(S)-5-(4-(Allyloxy)-4-methylpiperidin-1-yl)-6-(1-(tert-butoxy)-2-methoxy-2-oxoethyl)-7-methylimidazo[1,2-a]pyridine-2-carboxylic acid sodium salt: (S)-Ethyl 5-(4-(allyloxy)-4-methylpiperidin-1-yl)-6-(1-(tert-butoxy)-2-methoxy-2-oxoethyl)-7-methylimidazo[1,2-a]pyridine-2-carboxylate (450 mg, 0.923 mmol, 1 equiv) was dissolved in MeOH (9 mL). To this solution was added 1 N NaOH (1.02 mL, 1.015 mmol, 1.1 equiv). The reaction was stirred at 60° C. for 2 h. Upon cooling to ambient temperature, the reaction was concentrated in vacuo. The residue was then azeotroped with toluene to give a pale brown solid (S)-5-(4-(allyloxy)-4-methylpiperidin-1-yl)-6-(1-(tert-butoxy)-2-methoxy-2-oxoethyl)-7-methylimidazo[1,2-a]pyridine-2-carboxylic acid (400 mg, 92% yield) which was used as is for further reactions. LCMS (ESI, M+1): 474.35.

Intermediate 25

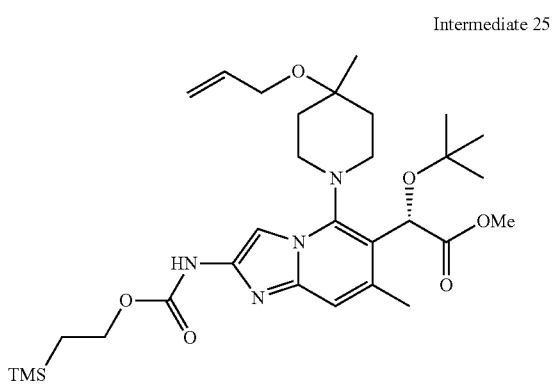 [SMILES: C=CCOC1(C)CCN(c2c([C@H](OC(C)(C)C)C(=O)OC)c(C)cc3nc(NC(=O)OCC[Si](C)(C)C)cn23)CC1]

(S)-Methyl 2-(5-(4-(allyloxy)-4-methylpiperidin-1-yl)-7-methyl-2-(((2-(trimethylsilyl)ethoxy)carbonyl)amino)imidazo[1,2-a]pyridin-6-yl)-2-(tert-butoxy)acetate: To a solution of (S)-5-(4-(allyloxy)-4-methylpiperidin-1-yl)-6-(1-(tert-butoxy)-2-methoxy-2-oxoethyl)-7-methylimidazo[1,2-a]pyridine-2-carboxylic acid (1.0 g, 2.112 mmol, 1 equiv) in THF (84 ml) was added triethylamine (0.59 mL, 0.100 mmol, 2 equiv) and diphenyl phosphorazidate (0.92 mL, 0.100 mmol, 2 equiv). After stirring 16 h, 2-(trimethylsilyl)ethanol (0.50 g, 4.22 mmol, 2 equiv) was added and the reaction was refluxed for 6 h. Upon cooling to ambient temperature, the reaction was concentrated in vacuo. The crude product was purified via silica gel flash chromatography (0-60% EtOAc [2% TEA]/hexane to provide (S)-methyl 2-(5-(4-(allyloxy)-4-methylpiperidin-1-yl)-7-methyl-2-(((2-(trimethylsilyl)ethoxy)carbonyl)amino)imidazo[1,2-a]pyridin-6-yl)-2-(tert-butoxy)acetate (1.0 g, 80%). LCMS (ESI, M+1): 589.4.

Intermediate 26

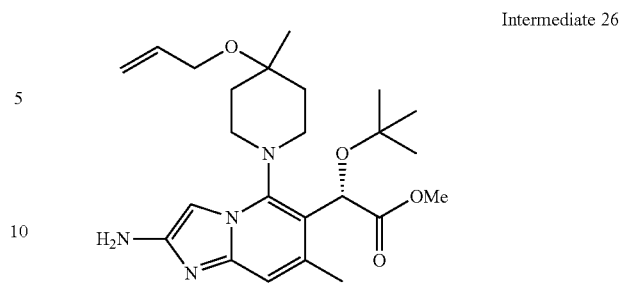

(S)-Methyl 2-(5-(4-(allyloxy)-4-methylpiperidin-1-yl)-2-amino-7-methylimidazo[1,2-a]pyridin-6-yl)-2-(tert-butoxy)acetate: A solution of (S)-methyl 2-(5-(4-(allyloxy)-4-methylpiperidin-1-yl)-7-methyl-2-(((2-(trimethylsilyl)ethoxy)carbonyl)amino)imidazo[1,2-a]pyridin-6-yl)-2-(tert-butoxy)acetate (0.85 g, 1.444 mmol) and TBAF (1.877 ml of a 1 M solution in THF, 1.877 mmol, 1.3 equiv) in THF (14 ml) was stirred for 3 h. The reaction was diluted with EtOAc, washed with water, dried (MgSO$_4$), and concentrated in vacuo to provide the product as a yellow foam (460 mg, 72%) which was used as is. LCMS(ESI, M+1): 445.3.

EXAMPLE 8

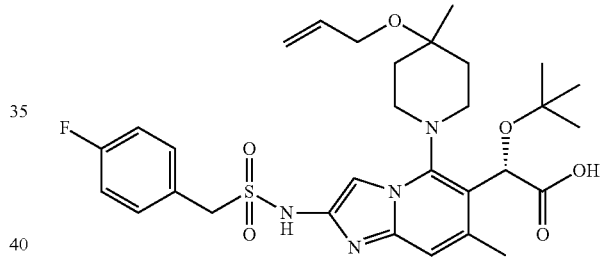

(S)-2-(5-(4-(Allyloxy)-4-methylpiperidin-1-yl)-2((4-fluorophenyl)methylsulfonamido)-7-methylimidazo[1,2-a]pyridin-6-yl)-2-(tert-butoxy)acetic acid: To a solution of (S)-methyl 2-(5-(4-(allyloxy)-4-methylpiperidin-1-yl)-2-amino-7-methylimidazo[1,2-a]pyridin-6-yl)-2-(tert-butoxy)acetate (30 mg, 0.067 mmol) and TEA (28.2 µL, 0.202 mmol, 3 equiv) in THF (0.45 mL) was added (4-fluorophenyl)methanesulfonyl chloride (28.2 mg, 0.135 mmol, 2 equiv) and stirred 18 h. To the reaction was then added water (0.45 mL), MeOH (0.45 mL), and LiOH monohydrate (160 mg, 4.05 mmol, 30 equiv). The reaction was heated at 50° C. for 2 h. Upon cooling to ambient temperature, the mixture was filtered and purified via preparative LC/MS with the following conditions: Column: XBridge C18, 19×mm, 5-µm particles; Mobile Phase A: 5:95 methanol: water with 10-mM ammonium acetate; Mobile Phase B: 95:5 methanol: water with 10-mM ammonium acetate; Gradient: 50-90% B over 20 minutes, then a 5-minute hold at 100% B; Flow: 20 mL/min to provide the product (40.6 mg, 100%). $^1$H NMR (500 MHz, DMSO-d$_6$) δ 7.43-7.36 (m, 2H), 7.27-7.07 (m, 4H), 6.11-5.99 (m, 1H), 5.89 (br. s., 1H), 5.37 (d, J=16.2 Hz, 1H), 5.15 (d, J=9.2 Hz, 1H), 4.60-4.55 (m, 2H), 4.00-3.95 (m, 2H), 3.70-3.62 (m, 2H), 2.99-2.91 (m, 1H), 2.66-2.58 (m, 1H), 2.39 (s, 3H), 1.88-1.63 (m, 4H), 1.24 (s, 3H), 1.18 (s, 9H); LCMS (ESI, M): 602.3.

EXAMPLE 9

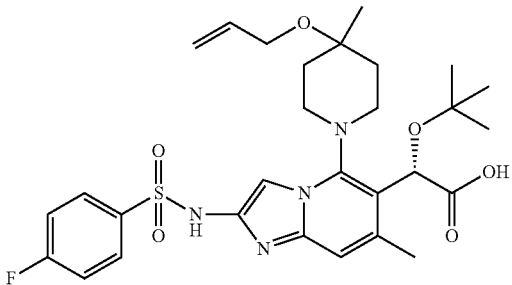 [SMILES: C=CCOC1(C)CCN(c2c([C@H](OC(C)(C)C)C(=O)O)c(C)cc3nc(NS(=O)(=O)c4ccc(F)cc4)cn23)CC1]

(S)-2-(5-(4-(Allyloxy)-4-methylpiperidin-1-yl)-2-(4-fluorophenylsulfonamido)-7-methylimidazo[1,2-a]pyridin-6-yl)-2-(tert-butoxy)acetic acid: To a solution of (S)-methyl2-(5-(4-(allyloxy)-4-methylpiperidin-1-yl)-2-amino-7-methylimidazo[1,2-a]pyridin-6-yl)-2-(tert-butoxy)acetate (20 mg, 0.045 mmol, 1 equiv) and TEA (18 μL, 0.135 mmol, 3 equiv) in THF (0.30 mL) was added 4-fluorobenzene-1-sulfonyl chloride (17.51 mg, 0.090 mmol, 2 equiv) and stirred 18 h. To the reaction was then added water (0.30 mL), MeOH (0.30 mL), and LiOH monohydrate (54 mg, 135 mmol, 30 equiv). The reaction was heated at 50° C. for 2 h. Upon cooling to ambient temperature, the mixture was filtered and purified via preparative LC/MS with the following conditions: Column: XBridge C18, 19×mm, 5-μm particles; Mobile Phase A: 5:95 methanol: water with 10-mM ammonium acetate; Mobile Phase B: 95:5 methanol: water with 10-mM ammonium acetate; Gradient: 50-90% B over 20 minutes, then a 5-minute hold at 100% B; Flow: 20 mL/min to provide the product (3.5 mg, 13%). $^1$H NMR (500 MHz, DMSO-$d_6$) δ 7.87 (br. s., 2H), 7.41-6.98 (m, 5H), 6.17-5.85 (m, 2H), 5.81 (br. s., 1H), 5.52-5.08 (m, 2H), 4.07-3.84 (m, 3H), 2.97 (br. s., 1H), 2.35 (br. s., 3H), 1.88-1.57 (m, 4H), 1.25 (br. s., 3H), 1.19-1.10 (m, 9H); LCMS (ESI, M): 588.2.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of Formula I

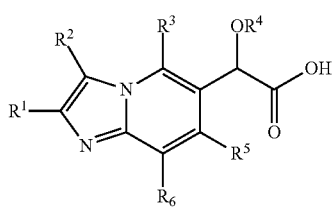

where:
$R^1$ is —CON($R^7$)($R^8$), —NHSO$R^7$, or ($R^7$)Ar$^2$;
$R^2$ is hydrogen or alkyl;
$R^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;
or $R^3$ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;
$R^4$ is alkyl or haloalkyl;
$R^5$ is hydrogen or alkyl;
$R^6$ is hydrogen or alkyl;
$R^7$ is Ar$^1$ or (Ar$^1$)alkyl;
$R^8$ is hydrogen or alkyl;
Ar$^1$ is phenyl substituted with 0-3 substituents selected from halo, cyano, alkyl, haloalkyl, alkoxy, haloalkoxy, and alkenyloxy; and
Ar$^2$ is pyrrolyl, furanyl, thienyl, pyrazolyl, isoxazolyl, isothiazolyl, imidazolyl, oxazolyl, thiazolyl, triazolyl, oxadiazolyl, or thiadiazolyl, and is substituted with 0-3 substituents selected from halo, cyano, alkyl, haloalkyl, alkoxy, haloalkoxy, and alkenyloxy;
or a pharmaceutically acceptable salt thereof.

2. A compound of claim 1 where $R^1$ is —CON($R^7$)($R^8$); $R^2$ is hydrogen or alkyl; $R^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl; or $R^3$ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl; $R^4$ is alkyl or haloalkyl; $R^5$ is hydrogen or alkyl; $R^6$ is hydrogen or alkyl; $R^7$ is (Ar$^1$)alkyl; $R^8$ is hydrogen or alkyl; and Ar$^1$ is phenyl substituted with 0-3 substituents selected from halo, cyano, alkyl, haloalkyl, alkoxy, haloalkoxy, and alkenyloxy; or a pharmaceutically acceptable salt thereof.

3. A compound of claim 1 where $R^1$ is ($R^7$)Ar$^2$; $R^2$ is hydrogen; $R^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl; or $R^3$ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl; $R^4$ is alkyl or haloalkyl; $R^5$ is alkyl; $R^6$ is hydrogen; $R^7$ is (Ar$^1$) alkyl; $R^8$ is hydrogen; and Ar$^1$ is phenyl substituted with 0-3 substituents selected from halo, cyano, alkyl, haloalkyl, alkoxy, haloalkoxy, and alkenyloxy; or a pharmaceutically acceptable salt thereof.

4. A compound of claim 1 where $R^1$ is ($R^7$)Ar$^2$.

5. A compound of claim 1 where $R^2$ is hydrogen, $R^4$ is alkyl, $R^5$ is alkyl, and $R^6$ is hydrogen.

6. A compound of claim 1 where $R^1$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl.

7. A compound of claim 1 where $R^3$ is piperidinyl substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl.

8. A compound of claim 1 where $R^4$ is alkyl.

9. A compound of claim 1 where $R^5$ is alkyl.

10. A compound of claim 1 where $R^7$ is $(Ar^1)CH_2$.

11. A compound of claim 1 selected from the group consisting of
- (S)-2-(tert-Butoxy)-2-(5-(4,4-dimethylpiperidin-1-yl)-2-((4-fluoro-3-methylbenzyl)carbamoyl)-7-methylimidazo[1,2-a]pyridin-6-yl)acetic acid;
- (S)-2-(tert-Butoxy)-2-(5-(4,4-dimethylpiperidin-1-yl)-2-(5-(4-fluorobenzyl)oxazol-2-yl)-7-methylimidazo[1,2-a]pyridin-6-yl)acetic acid;
- (S)-2-(tert-Butoxy)-2-(5-(4,4-dimethylpiperidin-1-yl)-2-(5-(4-fluorobenzyl)thiazol-2-yl)-7-methylimidazo[1,2-a]pyridin-6-yl)acetic acid;
- (S)-2-(2-(3-Benzyl-1,2,4-oxadiazol-5-yl)-5-(4,4-dimethylpiperidin-1-yl)-7-methylimidazo[1,2-a]pyridin-6-yl)-2-(tert-butoxy)acetic acid;
- (S)-2-(2-(5-Benzyl-1,3,4-oxadiazol-2-yl)-5-(4,4-dimethylpiperidin-1-yl)-7-methylimidazo[1,2-a]pyridin-6-yl)-2-(tert-butoxy)acetic acid;
- (S)-2-(tert-Butoxy)-2-(2-(4-chloro-5-(4-fluorobenzyl)-1H-imidazol-2-yl)-5-(4,4-dimethylpiperidin-1-yl)-7-methylimidazo[1,2-a]pyridin-6-yl)acetic acid;
- (S)-2-(tert-Butoxy)-2-(5-(4,4-dimethylpiperidin-1-yl)-2-(5-(4-fluorobenzyl)-1H-imidazol-2-yl)-7-methylimidazo[1,2-a]pyridin-6-yl)acetic acid;
- (S)-2-(5-(4-(Allyloxy)-4-methylpiperidin-1-yl)-2-((4-fluorophenyl)methylsulfonamido)-7-methylimidazo[1,2-a]pyridin-6-yl)-2-(tert-butoxy)acetic acid; and
- (S)-2-(5-(4-(Allyloxy)-4-methylpiperidin-1-yl)-2-(4-fluorophenylsulfonamido)-7-methylimidazo[1,2-a]pyridin-6-yl)-2-(tert-butoxy)acetic acid or a pharmaceutically acceptable salt thereof.

12. A composition useful for treating HIV infection comprising a therapeutic amount of a compound of claim 1 and a pharmaceutically acceptable carrier.

13. The composition of claim 12 further comprising a therapeutically effective amount at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

14. A method for treating HIV infection comprising administering a therapeutically effective amount of a compound of claim 1, or a pharmaceutically acceptable salt thereof, to a patient in need thereof.

15. The method of claim 14 further comprising administering a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

* * * * *